US00PP09898P

United States Patent [19]

Plate

[11] Patent Number: Plant 9,898

[45] Date of Patent: May 20, 1997

[54] ANTHURIUM PLANT NAMED FRANZISKA

[75] Inventor: Renate Plate, Bremen, Germany

[73] Assignee: Wolfgang Bock Pflanzenexport KG, Bremen, Germany

[21] Appl. No.: 560,473

[22] Filed: Nov. 17, 1995

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 5,696 3/1986 van der Laarse ..... Plt./88.1

P.P. 9,169 6/1995 Lamb et al. ..... Plt./88.1

*Primary Examiner*—James R. Feyrer

*Attorney, Agent, or Firm*—Foley & Lardner

[57] ABSTRACT

A new and distinct Anthurium plant named 'Franziska' particularly characterized by its round or elliptical red spathes, each with a twisted orange spadix, which are held straight above the foliage in the center of the plant. Its leaves are broad, moderately thick and somewhat glossy. The growth habit is very compact.

1 Drawing Sheet

The present invention comprises a new and distinct cultivar of Anthurium, botanically known as *Anthurium scherzerianum*, and referred to by the cultivar name 'Franziska'.

The new cultivar is a product of a breeding program carried out by the inventor Renate Plate, and is the result of a cross made by the inventor of selected but unnamed parentage made in Bremen, Germany. 'Franziska' was discovered from the progeny of the stated cross by the inventor. Asexual propagation by tissue culture conducted under the supervision of the inventor in Bremen, Germany was used to increase the number of plants for evaluation and has demonstrated the stability of the combination of characteristics from generation to generation.

The following observations, measurements and values describe plants grown in Apopka, Fla. under greenhouse conditions which closely approximate those generally used in horticultural practice.

The following traits have been repeatedly observed to be characteristics which in combination distinguish 'Franziska' from other *Anthurium scherzerianum* cultivars, and from the cultivar 'Shazzam', disclosed in U.S. Plant Pat. No. 9,169.

1. Plants of 'Franziska' produce many cupped elliptical red spathes, with a contrasting orange spadix. Plants of 'Shazzam', by comparison, produce fewer, larger red-orange spathes.

2. Unlike 'Shazzam', spathes of 'Franziska' are held straight above the foliage in the center of the plant.

3. The spathes of 'Franziska' are red, which darkens with age. The spadix becomes twisted with age.

4. The leaves of 'Franziska' are broad, stiff, leathery, moderately thick, with distinctive puckering of the leaf blade along the midrib. Leaves of 'Shazzam', by comparison, are longer and narrower.

5. The growth habit of 'Franziska' is very compact compared to that of 'Shazzam'.

All color references are measured against The Royal Horticultural Society Colour Chart. Colors are approximate as color depends on horticultural practices such as light level and fertilization rate, among others, without, however, any change in genotype.

The color photographic drawing comprises a top perspective view of the inflorescence and foliage of a plant of 'Franziska' in a 15.2 cm pot. The photograph was taken approximately 10 months after planting a 16-week-old liner obtained by tissue culture and grown under appropriate growing conditions. Colors are as accurate as possible with color illustrations of this type.

Origin: Seedling of selected parentage.

Classification: *Anthurium scherzerianum*, cv. 'Franziska'.

Propagation: Asexual production either by tissue culture or division.

Inflorescence: The spathe is tightly rolled around the spadix and emerges from the petiole sheath. The spathe is fully open about when the pedicel is fully elongated, approximately 19 cm above the soil surface. The color of the peduncle is greener than, but closest to 173 A, often becoming red 42 A-B near the base of the spathe.

*Spathe color.*—Upper Surface: 42 A; mature color 45 A. Lower Surface: Glossy, 42 A; mature color 45 C.

*Arrangement.*—The spathes stand up straight on tough wiry peduncles and open above the leaves in the center of the plant.

*Shape.*—The spathe is elliptical to round with an obtuse to cordate base and a cuspidate tip that is hooked. It is distinctly cupped when new and often reflexed with age. The spathes are approximately 6.4 cm to 8.0 cm long, approximately 5.4 cm to 7.7 cm in width, and approximately 1.2 cm in depth.

*Flowering time.*—After approximately 10 months from a 16 week old liner for an untreated plant having three growing points as illustrated in the photograph, and depending on season, approximately 4 to 6 inflorescences will be present. First flowers (2 to 3 ) can be expected approximately 4 months after planting a 16 week old liner.

Reproductive organs:

*Spadix.*—Size: Approximately 5.6 cm to 7.2 cm in length and approximately 6 mm in width. The spadix is straight when the spathe first unrolls, but becomes distinctly twisted with age. Color: The spadix is 40 B when new, and 30 C-D when fully emerged. Stamens: Anthers and filaments are minute, and not clearly visible. Pollen: 158 D in color. Pistil: Translucent, 40 D in color, protruding between the staminate flowers, firmly fixed to the main axil. The pistilate flowers extend approximately 0.5 mm beyond the staminate flowers.

General appearance: Under appropriate growing conditions, 'Franziska' attains a mature size of approximately 15.5 cm to 22 cm in height and approximately 41 cm to 44 cm. in width.

Leaves:

*Form.*—The leaf blade is broadly ovate with a cuspidate tip and a cordate base. The margins are entire. The midrib is straight over the length of the leaf. The leaf blade is distinctly puckered, and often folded upward from the midrib. The leaf margin is straight. The upper leaf surface is somewhat glossy, particularly on newly emerged leaves. The leaves are stiff, leathery, and moderately thick.

*Size.*—Leaf blades of a mature sized plant are approximately 13 cm to 15.5 cm in length and approximately 8.3 cm to 10 cm in width.

*Veins.*—Veins are sunken, and the leaf blade is often distinctly puckered or concave between veins. The midrib protrudes from the upper surface of the leaf for approximately ¾ the length of the leaf. Primary veins border the perimeter of the leaf.

*Petiole.*—The petiole is approximately 9.2 cm to 10.3 cm in height from the base of the petiole to the base of the leaf blade. The petiole is approximately 4.0 mm in diameter just below the geniculum, and straight. Two parallel ridges run the length of the upper surface of petiole.

*Petiole wings.*—Petiole wings are approximately 1.0 cm to 1.5 cm in length and approximately 6.0 mm in width at their midpoint The tips of the petiole wings are rounded. There is approximately 7.5 cm to 7.9 cm between the top of the wing and the base of the geniculum.

*Geniculum.*—The geniculum is approximately 4 mm to 11 mm in length, approximately 5 mm in diameter. The color is 146 D.

*Lobes.*—The leaf has two rounded lobes which extend past the petiole. The distance from the petiole/leaf juncture to the highest point on the lobes is approximately 1.2 cm.

*Color.*—Upper surface: Darker and greener than, but closest to 137 A. Lower surface: 146 D. Midrib, upper surface: 146 C. Midrib, lower surface: 147 C. Petiole: 146 A-B. Petiole wing: 146 A-B, bordered with 187D.

Roots: Greenish white fleshy roots with fine laterals. The roots are 187 A in color when located above the soil.

General observations: 'Franziska' produces cupped round or elliptical red spathes with a contrasting twisted orange spadix. The inflorescences are held straight above the leaves in the center of the plant. The leaves are broadly ovate, somewhat glossy, stiff, and often distinctly puckered along the midrib. The plant habit is very compact.

It is claimed:

1. A new and distinct cultivar of Anthurium plant named 'Franziska', as illustrated and described.

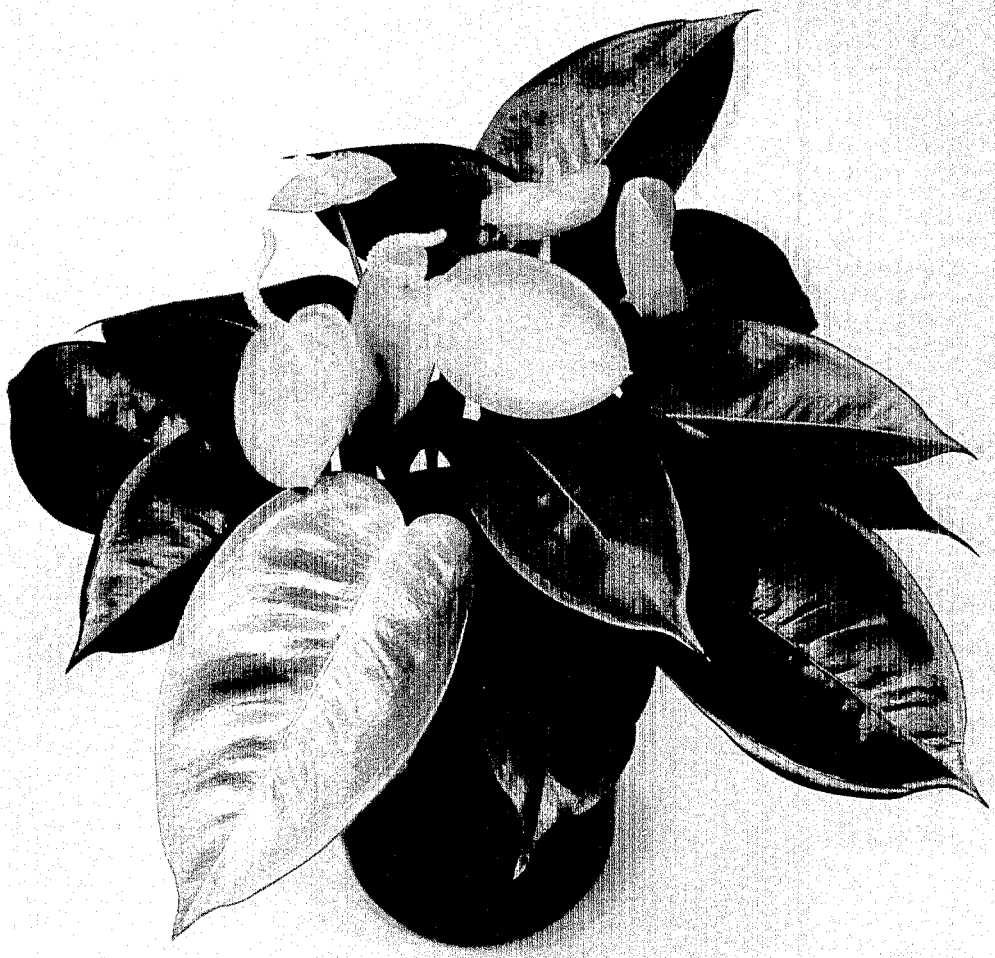

* * * * *